United States Patent [19]

Cramer

[11] Patent Number: 5,749,858
[45] Date of Patent: May 12, 1998

[54] METHOD OF USING AN ASPIRATION CATHETER

[75] Inventor: Bernhard M. Cramer, Wuppertal, Germany

[73] Assignee: Schneider (Europe) A.G., Bulach, Switzerland

[21] Appl. No.: 736,560

[22] Filed: Oct. 24, 1996

Related U.S. Application Data

[62] Division of Ser. No. 262,206, Jun. 20, 1994, Pat. No. 5,569,204.

[30] Foreign Application Priority Data

Jun. 24, 1993 [EP] European Pat. Off. ............. 93110061

[51] Int. Cl.⁶ ................................................. A61M 25/01
[52] U.S. Cl. ........................................................... 604/164
[58] Field of Search ................................. 604/48, 49, 51–53, 604/158, 164, 902; 606/159

[56] References Cited

U.S. PATENT DOCUMENTS

| | | |
|---|---|---|
| 4,445,509 | 5/1984 | Auth . |
| 4,493,696 | 1/1985 | Uldall ........................................ 604/164 |
| 4,759,349 | 7/1988 | Betz et al. .................................. 604/27 |
| 4,886,067 | 12/1989 | Palermo . |
| 4,944,729 | 7/1990 | Buckberg et al. . |
| 4,976,689 | 12/1990 | Buckbinder et al. . |
| 4,997,419 | 3/1991 | Lakatos et al. . |
| 4,998,916 | 3/1991 | Hammerslag et al. . |
| 4,998,919 | 3/1991 | Schnepp-Pesch et al. . |
| 5,011,488 | 4/1991 | Ginsburg . |
| 5,021,044 | 6/1991 | Sharkawy . |
| 5,120,308 | 6/1992 | Hess . |
| 5,156,596 | 10/1992 | Balbierz et al. . |
| 5,159,937 | 11/1992 | Tremulis . |
| 5,163,911 | 11/1992 | Sirimanne et al. . |
| 5,256,144 | 10/1993 | Kraus et al. . |
| 5,273,527 | 12/1993 | Schatz et al. . |
| 5,344,399 | 9/1994 | DeVries . |

FOREIGN PATENT DOCUMENTS

| | | |
|---|---|---|
| 0025704 | 3/1981 | European Pat. Off. . |
| 0177782 | 4/1986 | European Pat. Off. . |
| 0245211 | 11/1987 | European Pat. Off. . |
| 8910603.2 | 1/1990 | Germany . |
| 9004994 | 5/1990 | WIPO . |

*Primary Examiner*—Michael Buiz
*Assistant Examiner*—Kevin Truong
*Attorney, Agent, or Firm*—Peter C. Richardson; Lawrence C. Akers; Philip C. Strassburger

[57] ABSTRACT

An aspiration catheter arrangement for aspiration of thrombi and emboli from blood vessels has a central catheter (2) and an outside catheter (1) surrounding it coaxially. A guide wire (4) and a dilator (3) are provided for inserting the catheter arrangement into a vessel and for dilating same. A blood clot is removed by means of a vacuum applied to the central catheter (2). If the central catheter (2) becomes clogged by the blood clot during the aspiration procedure, the central catheter (2) can be extracted out of the outside catheter (1) and replaced by a new central catheter (2). This new central catheter (2) can be connected to the aspiration device and the process is then continued. Instead of inserting a new central catheter (2), the aspiration process can also be continued through the outside catheter (1) by connecting the latter to the aspiration device after removing the central catheter (2).

12 Claims, 2 Drawing Sheets

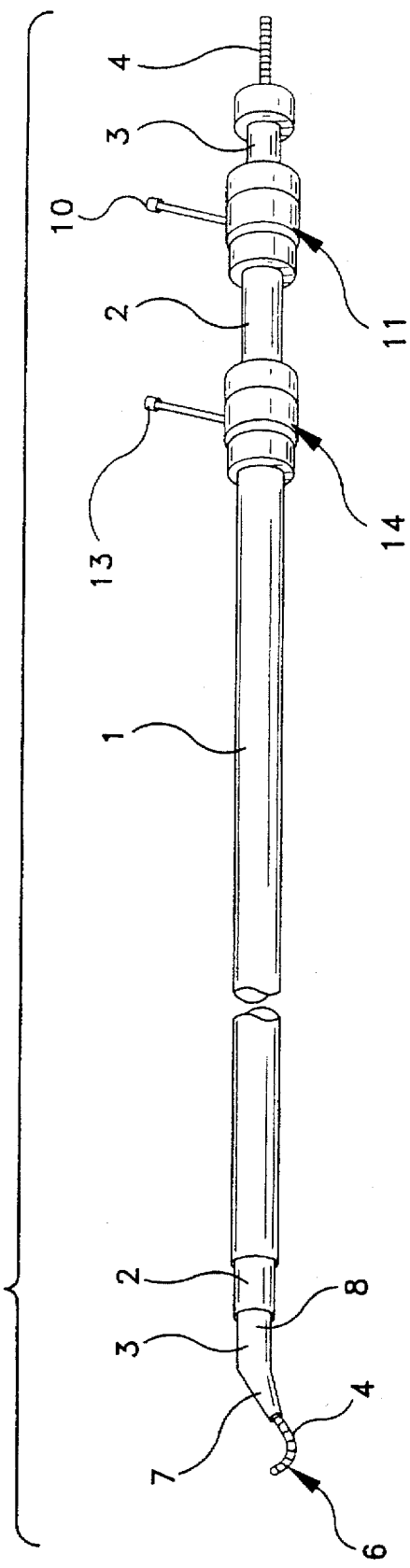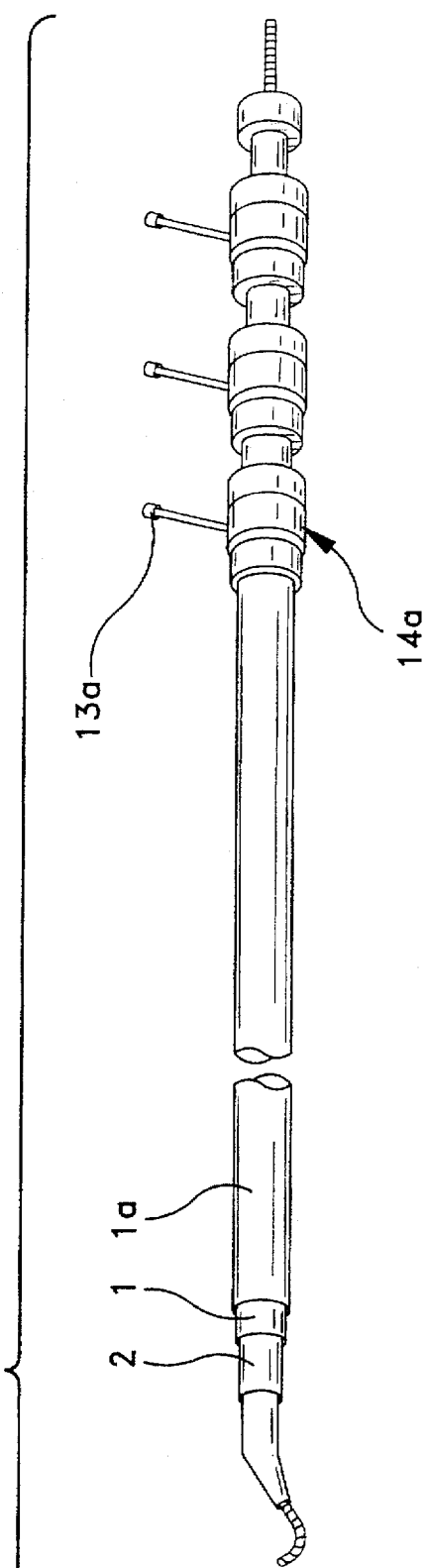

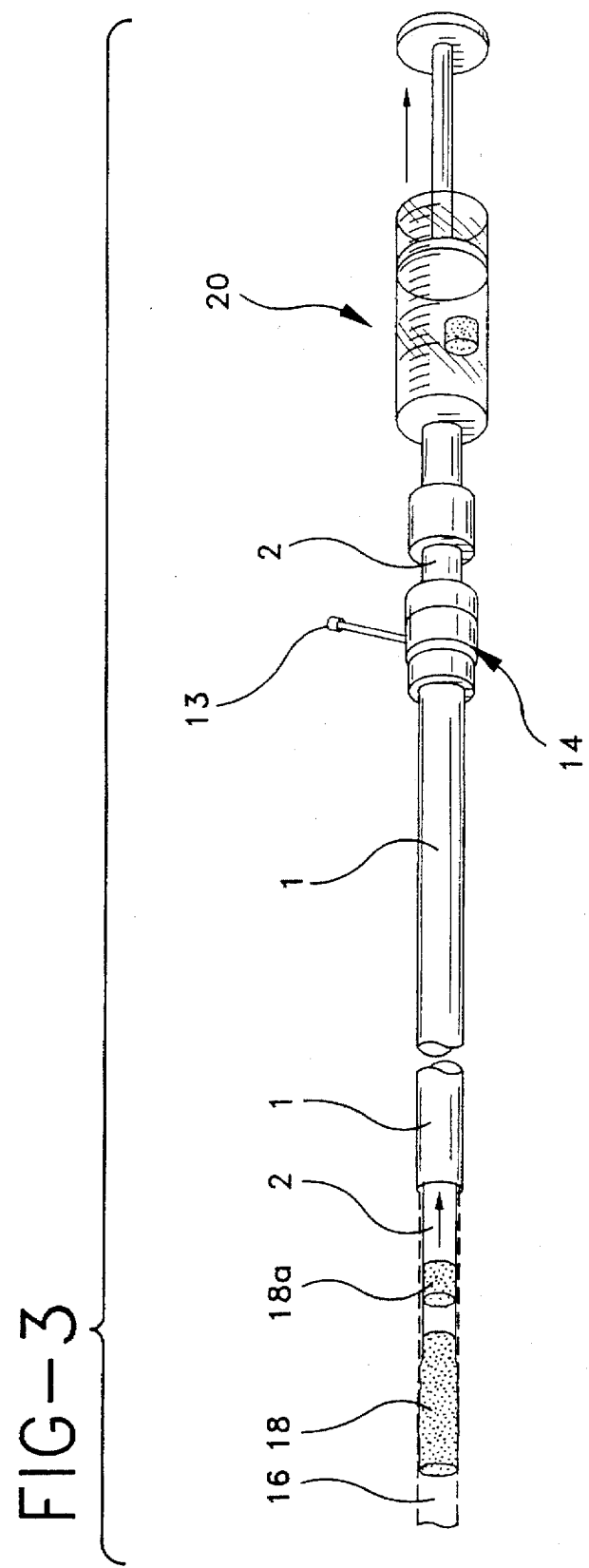

METHOD OF USING AN ASPIRATION CATHETER

This is a division of application Ser. No. 08/262,206, filed on Jun. 20, 1994, now U.S. Pat. No. 5,569,204.

BACKGROUND OF THE INVENTION

This invention concerns an aspiration catheter arrangement.

Catheter arrangements of the generic type are used to remove thrombi and emboli by guiding the catheter through a blood vessel up to the blood clot that is to be removed and attaching it at the proximal end to a suction device. The vacuum prevailing in the catheter then aspirates the blood clot. A major problem in aspiration of blood clots with such aspiration catheters is that the blood clots can easily clog the aspiration catheter, especially if the diameter of the clot is larger than the diameter of the catheter itself. The catheter must then be retracted from the blood vessel in order to remove such a blockage. Then either the clogged catheter is cleaned outside of the patient's body or a new unused catheter is inserted into the vessel. In either case, however, a catheter must be introduced at least twice into the blood vessel in question.

However, any movement of a catheter in a blood vessel poses a threat to the vascular wall. Even if the catheter is advanced with the help of a dilator in order to reduce the danger of injury to the vascular wall, any such movement must be very slow. The cleaning operation, which is tedious anyway, is thus prolonged further. In addition, the position of the blood clot within the vascular system must be relocated again each time the catheter is inserted. If a previously unused catheter is inserted, it must be completely sterile just like the first catheter used.

Various embodiments of catheters have become known for reducing the danger of blockage of such aspiration catheters in aspirating blood clots. For example, European Patent No. 177,782 discloses an apparatus having a rotating shaft for transluminal removal of thrombi. The fibrin is thought to be extracted from the thrombus by this rotating shaft, so the thrombus is broken up and the blood can flow freely again. A special rounded tip on the shaft itself and the catheter around the shaft on the outside prevent the shaft from injuring the vascular wall. The pressure at the treatment site can be monitored through the catheter and medication can also be introduced through it. In addition, fluid can also be aspirated continuously through the catheter. However, the fibrin that becomes wrapped around the shaft must be removed mechanically from the shaft, for which purpose the shaft must be removed from the catheter.

In addition, European Patent No. 367,982 discloses a catheter arrangement that is referred to as a device for percutaneous removal of thrombi and emboli and has a rotating propeller for disintegrating the thrombus during aspiration. With the help of a suction device, the blood clots can be aspirated continuously. However, both embodiments have some disadvantages. For example, the rotating body and the drive shaft greatly reduce the cross-sectional area of the catheter available for aspiration. In addition, such catheters have a relatively complicated design and are expensive to manufacture due to the rotating body and the drive shaft. In particular, however, these instruments do not include a dilator, so they must be inserted into the blood vessel with insertion instruments that must be kept on hand for this purpose. Again, because of the absence of a dilator, there is the danger of injury to the vascular wall due to the edge of the distal catheter orifice when these instruments are advanced through a vessel. Furthermore, injury to surrounding vascular parts cannot be ruled out entirely due to a tip or a rotating head that disintegrates the thrombus. When using an insertion aid, the blood vessel is first punctured with a hollow aspirating needle. Then a short, relatively stable guide wire is advanced into the blood vessel in the hollow aspirating needle. Next, a conical dilator that receives the guide wire in a central longitudinal bore is advanced over this short guide wire. The conical dilator enlarges the puncture site to the extent that the insertion catheter can be advanced over the dilator and in close proximity to it. The dilator and the insertion catheter are closely paired and their diameters must be coordinated such that the aspiration catheter can be advanced into the blood vessel through the insertion catheter.

Such embodiments of catheters are also very expensive for a single use. However, if they are used repeatedly, the entire catheter arrangement must be cleaned and resterilized in a tedious procedure. However, repeated use is associated with certain risks because such an arrangement is subject to a certain amount of wear, and repeated sterilization can lead to changes in the material. In addition, the distal end of such a catheter arrangement is stiff due to the drive shaft, which thus makes it difficult to guide this catheter around tight curve radii. Finally, such devices in principle have a relatively large outside diameter so that only vessels with a large enough lumen are accessible to them.

German Utility Patent No. 8910603.2 discloses a device for removing blood clots from veins and arteries. This device has an inside catheter that is provided with an inflatable balloon on its distal end (Fogarty catheter). This inside catheter is surrounded by a sluice catheter having a radially expandable end piece. The sluice catheter is in turn surrounded by an outside catheter. To remove blood clots, the device is inserted percutaneously into the blood vessel with the help of an insertion set in the well-known Seldinger technique. Next, the uninflated balloon on the end of the inside catheter is advanced through the blood clot and inflated. The thrombus is then pulled mechanically into the enlarged end piece of the sluice catheter by pulling on the inside catheter with the inflated balloon. Next the thrombus is expressed by collapsing the radially expandable end piece and is removed from the blood vessel by mechanical extraction of the sluice catheter together with the inside catheter.

Due to the radially expandable sluice catheter, this device has the advantage that it can be used to remove blood clots that are larger in diameter than the sluice catheter. However, this device is limited to applications where blood clots are to be removed from a vessel in pieces. Although a vacuum can be applied to the sluice catheter as a supportive measure, this device is nevertheless unsuitable for continuous removal of blood clots by aspiration. The fibrin of the thrombus becomes stuck in the expandable mesh at the end of the sluice catheter in suction and can only be retained there due to the vacuum and cannot be aspirated continuously.

The sluice catheter also has a very small lumen in the area of its distal end, because it must support the mesh of the expandable end piece in this area, and the wall must be designed with a thickness suitable for transmitting the shearing and tensile forces needed to move this mesh.

Another disadvantage of such a device can be seen in the fact that the sluice catheter and the outside catheter are designed to be relatively stiff at least in the area of their distal ends due to the expandable mesh. Therefore, this device can be maneuvered only through vascular convolutions having a sufficiently large radius of curvature. However, convoluted vascular passages cannot be crossed or reached with such a device. In addition, there is also the danger of injury to the blood vessels if the mesh attached to the distal end of the sluice catheter is not enlarged in the correct manner.

Thus, the object of this invention is to create a catheter arrangement for continuous aspiration of blood clots that can be used without separate insertion instruments and has a simple and uncomplicated design, is easy to use, can be manufactured inexpensively and will allow a high rate of work even when a blockage occurs in the aspiration catheter and is also gentle with regard to the stress on the blood vessels into which it is inserted and permits complete removal even of blood clots larger than the diameter of the aspiration catheter. Furthermore, the aspiration cross section of the catheter should be large in relation to the outside diameter, the catheter should be flexible enough so it can be guided even through tight curves in the path of the vessel and can be advanced even into small vessels but nevertheless has a high rigidity at the proximal end for advancing it and has a smooth intake orifice without any obstacles for the thrombus.

The aspiration catheter arrangement according to this invention includes an outside catheter whose distal end can be advanced up to the distal end of the central catheter.

Due to such a design of the aspiration catheter arrangement, the latter can be inserted percutaneously through a small puncture orifice into a blood vessel without the use of insertion instruments. The distal ends of the two catheters are normally aligned during insertion. However, it is also conceivable for one of the two catheters to project beyond the other at the distal end. It is thus easy to vary the rigidity of the catheter arrangement and its diameter at the distal end without any negative effect on the high rigidity wanted in the area of the proximal end of the catheter arrangement or the large aspiration cross section. To remove a blood clot, the outside catheter is inserted into the blood vessel through the puncture site in the known way together with the central catheter with the dilator and guide wire also inserted, and then it is advanced further in the blood vessel as far as the blood clot targeted for removal. The dilator and the guide wire are removed next.

An attempt is then made to aspirate the blood clot by connecting the central catheter to a suction device. As long as the central catheter is not clogged by the aspirated blood clot, this aspiration technique does not differ from traditional aspiration methods. However, if the blood clot does clog the central catheter—which is highly probably with large thrombi—essentially at least four different possible solutions may be considered:

1. The clogged central catheter is retracted out of the outside catheter and replaced by a new central catheter which is then advanced in the outside catheter, and the aspiration process is continued with the new central catheter.
2. The clogged central catheter is retracted out of the outside catheter and the outside catheter is connected instead to the aspiration device so the aspiration process is continued through the outside catheter.
3. The clogged central catheter is retracted out of the outside catheter, the blockage is removed from the central catheter and the same central catheter is inserted again and the aspiration process is continued with the same central catheter.
4. After a blockage in the central catheter, the outside catheter is advanced while maintaining the vacuum in the central catheter, and in this way the entire blood clot is drawn into the outside catheter and then removed by extracting both of the catheters at the same time.

This procedure of inserting and retracting the central catheter described in points 1 to 3 can be repeated several times due to the presence of an outside catheter without causing any additional stress on the blood vessels. In addition, the central catheter can also be extracted and reinserted very rapidly through the outside catheter. Due to the fact that the outside catheter remains in the vessel, the central catheter is reliably guided back to the same treatment site. No time is lost in locating the treatment site again. The proposed catheter also has a very simple design and consists only of two tubes, one of which fits inside the other, with a dilator on the inside. The parts need not withstand high loads. Therefore, the new catheter is very simple to manufacture.

Another important advantage of such a catheter arrangement is that it can be manufactured very inexpensively in comparison with catheter arrangements having a rotating body. Furthermore, there need not be any drive mechanism for the rotating body. Likewise, the cross-sectional area available inside the catheter is not restricted unnecessarily. In addition, use of such a catheter arrangement as a disposable unit is made possible by the low cost of manufacturing it, so this eliminates time-consuming and tedious resterilization of the used catheter arrangement which is not always entirely without problems in terms of the materials of which the catheter is made. In general, it is difficult to reliably clean the inside lumen of a catheter.

In order to allow the outside catheter to be connected to an aspiration device, it is proposed in another preferred embodiment that the outside catheter have a connecting part in the area of its proximal end by means of which it can be connected to the aspiration device. By connecting the outside catheter to an aspiration device, it is possible to apply a vacuum to the outside catheter itself after retracting the central catheter from the outside catheter, and thus the blood clot or any remaining residues thereof can be removed through the outside catheter.

Another embodiment of the catheter arrangement includes several outside catheters. This makes it simple to use the innermost of the outside catheters for aspiration after retracting the central catheter. Due to such a design, several catheters can be used in succession without having to insert a new central catheter each time. On the other hand, a high rigidity can thus be achieved on the proximal end of the catheter arrangement without impairing the flexibility of the distal end, its large aspiration cross section and small outside diameter.

In another preferred embodiment of this invention, the outside diameter of the central catheter corresponds at least approximately to the inside diameter of the outside catheter, or when there are several outside catheters, the outside diameter of the innermost of the outside catheters will correspond to the inside diameter of the next outermost outside catheter. This yields the result that the outside diameter of the outside catheter is only insignificantly larger than the outside diameter of the central catheter, and this does not unnecessarily increase the diameter of the catheter arrangement. In addition, the central catheter is guided in the outside catheter due to such a design. It is self-evident that the diameters should be selected in such a way that the catheters can easily be shifted axially with respect to each other. In addition, the close proximity, the wall thickness of the two catheters or the various catheters may be varied, and specifically, the wall thickness may be so thin that the wall thickness of one catheter alone would not have enough rigidity for reliable insertion into a blood vessel but when one catheter is inserted into the other, together they have enough rigidity or buckling resistance.

In order to support this displaceability, Teflon is proposed as the material for the catheter in another embodiment.

Another embodiment provides for the tip of the dilator to form an angle with the axis of the shaft and for the tip of the dilator to be capable of rotating in different directions by rotating the dilator at its proximal end. Thus, the dilator can be controlled in such a way that even convoluted vascular passages can be reached safely and reliably.

Finally, in another embodiment, the tip of the dilator can be bent with respect to the axis of the shaft. In this way, the tip can be designed so it is straight or can be controlled individually.

One embodiment of this invention is explained in greater detail below with reference to the accompanying figures which show the following:

FIG. 1 shows a perspective view of the aspiration catheter arrangement with the dilator and guide wire inserted.

FIG. 2 shows a perspective view of the aspiration catheter arrangement in an embodiment with two outside catheters.

FIG. 3 shows a perspective schematic view of the aspiration catheter arrangement in aspiration of a blood clot.

FIG. 1 shows a perspective view of the aspiration catheter arrangement. The essential parts of this catheter arrangement include an outside catheter 1, a central catheter 2, a dilator 3 and a guide wire 4. The guide wire 4 is inserted into dilator 3. Guide wires 4 are held flexibly on their distal end so they will definitely not injure the vascular wall when advanced in the vessel. In addition, however, guide wires 4 also have the greatest possible torsional rigidity and their distal ends can be bent permanently. With the help of these properties, the guide wire 4 can be guided into a branch in the vascular system, for example, from its proximal end.

The dilator 3 in turn has a tubular design and a conical tip 7 at its distal end, such that the axis of the tip forms an angle with the axis of shaft 8. This tip 7 can be bent with respect to the axis of shaft 8 and thus can be adapted individually to the given situation. By rotating the dilator 3 at its proximal end, the tip 7 can be rotated in different directions. The central catheter 2 encloses the dilator 3 for most of its length and has a connecting part 10 on its proximal end—for introducing a contrast medium, for example, with a hemostatic valve 11. The central catheter 2 is in turn surrounded by outside catheter 1 for most of its length, and outside catheter 1 also has a connecting part 13 and hemostatic valve 14 at its distal end.

FIG. 2 shows another embodiment of the aspiration catheter arrangement, where the difference in comparison with the embodiment according to FIG. 1 consists of a second outside catheter 1a surrounding the first outside catheter 1 along most of its length. This outside catheter 1a also has a connecting part 13a and hemostatic valve 14a at its proximal end. Embodiments having additional outside catheters are of course also possible.

FIG. 3 illustrates how a blood clot is removed. With the catheter arrangement illustrated in this figure, the central catheter 2 is shown in longitudinal section in the foremost distal area in order to better illustrate it. Introducing such a catheter arrangement into a blood vessel is a standard procedure, so only the most important points are discussed here. First, guide wire 4 is inserted into blood vessel 16 through a puncture in the skin and is advanced to the vicinity of the blood clot 18, 18a to be removed. Next, dilator 3 is inserted together with central catheter 2 and outside catheter 1 into blood vessel 16 and advanced as far as necessary, whereby the dilator 3 projects slightly beyond central catheter 2 distally in order to enlarge the puncture site. Hemostatic valves 11, 14 on the proximal ends of the catheters 1, 2 prevent blood from escaping through the catheter arrangement.

The two catheters 1, 2 can be inserted and advanced in different ways. For example, catheters 1, 2 and dilator 3 can be inserted together with their distal ends aligned. However, it is also possible for the distal end of one catheter, preferably the central catheter 2, to be upstream from the distal end of the other catheter in insertion. In this way, the rigidity and the diameter of the catheter arrangement can be varied in the area of its distal end.

Finally, the central catheter 2 can be advanced all the way up to blood clot 18 to be removed. At this point at the latest, the dilator 3 together with the guide wire 4 is retracted from the central catheter 2 and removed. The blood clot 18, 18a is then removed by aspiration in the traditional manner. To do so, hemostatic valve 11 of the central catheter 2 is removed and central catheter 2 is connected to a manual suction device 20 at connecting part 10. Instead of a manual suction device 20, other solutions are of course also possible, such as an electric pump. Then the blood clot 18, 18a can be aspirated continuously by the vacuum prevailing in central catheter 2. If central catheter 2 becomes clogged by the blood clot 18 or a part 18a thereof during aspiration, central catheter 2 can be withdrawn completely from outside catheter 1 and cleaned or a new central catheter can be inserted into outside catheter 1 and work can be continued after connecting it to suction device 20. However, it is also possible to continue the suction process after removing the central catheter 2 with the outside catheter 1 by removing its hemostatic valve 14 and connecting the proximal end to the suction device 20.

Another variant for removing the blood clot 18, 18a consists of attempting to pull it as a whole into the outside catheter 1 by means of the vacuum applied to the central catheter 2 and by a forward movement of the outside catheter 1 and then removing it by simultaneously retracting both catheters 1, 2, preferably while maintaining the vacuum on central catheter 2. This is no problem since the blood clot 18, 18a is not exposed to any more friction in retracting the catheter arrangement from blood vessel 16 after the blood clot has been drawn into the outside catheter 2 and therefore it can be removed safely and reliably. This method is especially effective when a vacuum is also applied to the outside catheter 1 through connecting part 13 in order to hold the thrombus securely in or on outside catheter 1.

When using an aspiration catheter arrangement like that shown in FIG. 2, still other variants of this aspiration technique are also possible. For example, after the central catheter 2 becomes clogged and is removed, the aspiration process is continued with the innermost outside catheter 1 (FIG. 2) and if this outside catheter 1 becomes clogged and is removed, work can be continued with the next outside catheter 1a (FIG. 2).

In contrast with traditional devices for removing thrombi and emboli, such an aspiration catheter arrangement has the great advantage that work can be continued after a brief interruption if central catheter 2 becomes clogged. In the past, blockage of the catheter meant that it had to be taken out of the blood vessel. If the blood clot was not yet completely removed at the time of the blockage of the catheter, a new catheter would have to be introduced. However, the same problems are encountered again each time a catheter is inserted. Thus, additional stress is placed on the patient's blood vessels and the catheter must again be guided cautiously to the proper location in the blood vessel. This is a very tedious procedure especially when the blood clot is a great distance from the puncture site. Furthermore, valuable time is lost unnecessarily in such a case.

In conclusion, it should be pointed out that a blood clot can be removed in the shortest possible amount of time by using the aspiration catheter arrangement according to this invention and the patient's blood vessels can be safeguarded in this way.

I claim:

1. A method of aspirating a blood vessel comprising:
   (a) providing an aspiration device comprising:
      (i) an outer catheter having a proximal end and a distal end, and
      (ii) an inner catheter removably configured at least partially within the outer catheter, adapted for removal from the proximal end of the outer catheter, and having a proximal end and a distal end;
   (b) inserting the aspiration device into a blood vessel and advancing the aspiration device adjacent a treatment site;
   (c) aspirating thrombus and/or emboli through the inner catheter until the inner catheter becomes clogged;
   (d) after the inner catheter becomes clogged, removing the inner catheter through the proximal end of the outer catheter while at least part of the outer catheter remains in the blood vessel;
   (e) cleaning the clogged inner catheter to provide a cleaned inner catheter;
   (f) inserting the cleaned inner catheter into the outer catheter through the proximal end of the outer catheter while at least part of the outer catheter remains in the blood vessel; and
   (g) continuing to aspirate thrombus and/or emboli through the cleaned inner catheter.

2. The method of claim 1 wherein the aspiration device is inserted into the blood vessel with the distal end of the outer catheter and the distal end of the inner catheter aligned.

3. The method of claim 1 wherein the aspiration device is inserted into the blood vessel with the distal end of the inner catheter extending distally relative the distal end of the outer catheter.

4. The method of claim 1 wherein the aspiration device is inserted into the blood vessel within the distal end of the outer catheter extending distally relative the distal end of the inner catheter.

5. A method of aspirating a blood vessel comprising:
   (a) providing an aspiration device comprising:
      (i) an outer catheter having a proximal end and a distal end, and
      (ii) an inner catheter removably configured at least partially within the outer catheter, adapted for removal from the proximal end of the outer catheter, and having a proximal end and a distal end;
   (b) inserting the aspiration device into a blood vessel and advancing the aspiration device adjacent a treatment site;
   (c) aspirating thrombus and/or emboli through the inner catheter until the inner catheter becomes clogged;
   (d) after the inner catheter becomes clogged, removing the inner catheter through the proximal end of the outer catheter while at least part of the outer catheter remains in the blood vessel; and
   (e) aspirating thrombus and/or emboli through the outer catheter.

6. The method of claim 5 wherein the aspiration device is inserted into the blood vessel with the distal end of the outer catheter and the distal end of the inner catheter aligned.

7. The method of claim 5 wherein the aspiration device is inserted into the blood vessel with the distal end of the inner catheter extending distally relative the distal end of the outer catheter.

8. The method of claim 5 wherein the aspiration device is inserted into the blood vessel within the distal end of the outer catheter extending distally relative the distal end of the inner catheter.

9. A method of aspirating a blood vessel comprising:
   (a) providing an aspiration device comprising:
      (i) an outer catheter having a proximal end and a distal end, and
      (ii) a first inner catheter removably configured at least partially within the outer catheter, adapted for removal from the proximal end of the outer catheter, and having a proximal end and a distal end;
   (b) inserting the aspiration device into a blood vessel and advancing the aspiration device adjacent a treatment site;
   (c) aspirating thrombus and/or emboli through the first inner catheter until the first inner catheter becomes clogged;
   (d) after the first inner catheter becomes clogged, removing the first inner catheter through the proximal end of the outer catheter while at least part of the outer catheter remains in the blood vessel;
   (e) providing a second inner catheter adapted for insertion into the outer catheter;
   (f) inserting the second inner catheter through the proximal end of the outer catheter while at least part of the outer catheter remains in the blood vessel; and
   (g) aspirating thrombus and/or emboli through the second inner catheter.

10. The method of claim 9 wherein the aspiration device is inserted into the blood vessel with the distal end of the outer catheter and the distal end of the first inner catheter aligned.

11. The method of claim 9 wherein the aspiration device is inserted into the blood vessel with the distal end of the first inner catheter extending distally relative the distal end of the outer catheter.

12. The method of claim 9 wherein the aspiration device is inserted into the blood vessel within the distal end of the outer catheter extending distally relative the distal end of the first inner catheter.

* * * * *